(12) United States Patent
Neukom et al.

(10) Patent No.: US 9,209,327 B2
(45) Date of Patent: Dec. 8, 2015

(54) SOLID-STATE PHOTODETECTOR PIXEL AND PHOTODETECTING METHOD

(71) Applicant: MESA Imaging AG, Zurich (CH)

(72) Inventors: Simon Neukom, Hittnau (CH); Michael Lehmann, Winterthur (CH); Rolf Kaufmann, Zurich (CH); Thierry Oggier, Zurich (CH)

(73) Assignee: Heptagon Micro Optics Pte. Ltd., Singapore (SG)

( * ) Notice: Subject to any disclaimer, the term of this patent is extended or adjusted under 35 U.S.C. 154(b) by 121 days.

(21) Appl. No.: 14/161,053

(22) Filed: Jan. 22, 2014

(65) Prior Publication Data

US 2014/0203389 A1    Jul. 24, 2014

Related U.S. Application Data (60) Continuation of application No. 12/987,669, filed on Jan. 10, 2011, now abandoned, which is a division of application No. 11/658,516, filed as application No. PCT/CH2005/000436 on Jul. 25, 2005, now Pat. No. 7,897,928.

(30) Foreign Application Priority Data

Jul. 26, 2004    (EP) .................................. 04405475

(51) Int. Cl.
*H01L 31/02*    (2006.01)
*H01L 27/14*    (2006.01)
(Continued)

(52) U.S. Cl.
CPC .......... *H01L 31/0232* (2013.01); *H01L 27/148* (2013.01); *H01L 27/14601* (2013.01); *H01L 27/14623* (2013.01); *H01L 31/02005* (2013.01)

(58) Field of Classification Search
CPC ..................... H01L 31/0232; H01L 31/02005; H01L 27/148; H01L 27/14623; H01L 27/14601
See application file for complete search history.

(56) References Cited

U.S. PATENT DOCUMENTS 5,442,169 A    8/1995    Kunz
5,459,323 A    10/1995    Morgan
(Continued)

FOREIGN PATENT DOCUMENTS

EP    0 911 667 A1    4/1999
EP    1085315 A1    3/2001
(Continued)

OTHER PUBLICATIONS

International Search Report from International Application No. PCT/CH2005/000436, mailed on Nov. 16, 2005.
(Continued)

*Primary Examiner* — Casey Bryant
(74) *Attorney, Agent, or Firm* — Fish & Richardson P.C.

(57) ABSTRACT

A pixel is formed in a semiconductor substrate (S) with a plane surface for use in a photodetector. It comprises an active region for converting incident light (In) into charge carriers, photogates (PGL, PGM, PGR) for generating a lateral electric potential ($\Phi(x)$) across the active region, and an integration gate (IG) for storing charge carriers generated in the active region and a dump site (Ddiff). The pixel further comprises separation-enhancing means (SL) for additionally enhancing charge separation in the active region and charge transport from the active region to the integration gate (IG). The separation-enhancing means (SL) are for instance a shield layer designed such that for a given lateral electric potential ($\Phi(x)$), the incident light (In) does not impinge on the section from which the charge carriers would not be transported to the integration gate (IG).

17 Claims, 12 Drawing Sheets

(51) Int. Cl.
 H01L 31/0232 (2014.01)
 H01L 27/146 (2006.01)
 H01L 27/148 (2006.01)

(56) References Cited

U.S. PATENT DOCUMENTS

| | | | |
|---|---|---|---|
| 5,856,667 | A | 1/1999 | Spirig et al. |
| 5,891,656 | A | 4/1999 | Zarling et al. |
| 5,986,297 | A * | 11/1999 | Guidash et al. ............... 257/223 |
| 6,395,558 | B1 * | 5/2002 | Duveneck et al. ............ 436/172 |
| 6,483,096 | B1 * | 11/2002 | Kunz et al. ................ 250/214 R |
| 6,537,829 | B1 | 3/2003 | Zarling et al. |
| 7,034,317 | B2 | 4/2006 | Olszak et al. |
| 7,279,338 | B2 | 10/2007 | Kim et al. |
| 7,508,505 | B2 * | 3/2009 | Lustenberger et al. ....... 356/317 |
| 2001/0035568 | A1 | 11/2001 | Shyu |
| 2003/0234410 | A1 * | 12/2003 | Takeuchi et al. .............. 257/258 |
| 2004/0008394 | A1 | 1/2004 | Lange et al. |
| 2004/0028567 | A1 | 2/2004 | Parce et al. |
| 2005/0023439 | A1 | 2/2005 | Cartlidge et al. |
| 2006/0108611 | A1 * | 5/2006 | Seitz ........................... 257/222 |
| 2009/0014658 | A1 * | 1/2009 | Cottier et al. ............ 250/370.08 |

FOREIGN PATENT DOCUMENTS

| | | |
|---|---|---|
| EP | 1152261 A1 | 11/2001 |
| EP | 1 162 827 A2 | 12/2001 |
| EP | 1 746 410 A1 | 1/2007 |
| JP | 2001267544 A | 9/2001 |
| WO | 02/12945 A2 | 2/2002 |

OTHER PUBLICATIONS

Buettgen, B. et al., "Demonstration of a Novel Drift Field Pixel Structure for the Demodulation of Modulated Light Waves with Application in Three-Dimensional Image Capture," SPIE vol. 5302, Apr. 2004, pp. 9-20.

Lakowicz, J., "Principles of Fluorescence Spectroscopy," Kluwer Academic and Plenum Publishers, New York, 1999, pp. 1-24.

Lange, R. et al., "Solid-State Time-of-Flight Range Camera," IEEE Journal of Quantum Electronics, vol. 37, No. 3, Mar. 2001, pp. 390-397.

Miyagawa, R. et al., "CCD-Based Range-Finder Sensor," IEEE Transactions on Electron Devices, vol. 44, No. 10, Oct. 1997, pp. 1648-1652.

Rowe, H. M. et al., "Elimination of Fluorescence and Scattering Backgrounds in Luminescence Lifetime Measurements Using Gated-Phase Fluorometry," Anal. Chem. 2002, vol. 74, pp. 4821-4827.

Theuwissen, A. J. P., "Solid State Imaging with Charge Coupled Devices," Kluwer Academic Publishers, Dordrecht, 1995, pp. 7-51.

Elson, D.S. et al., "Fluorescence Lifetime Imaging with a Blue Picosecond Diode Laser," Optical Society of America, Optics Letters, vol. 27, No. 16, 2002, pp. 1409-1411.

Elson, D. et al., "Time-domain fluorescence lifetime imaging applied to biological tissue," The Royal Society of Chemistry and Owner Societies, Photochem. Photobiol. Sci., 2004, pp. 795-801.

Esposito, A. et al., "Fluorescence Lifetime Imaging Microscopy," John Wiley & Sons, Inc., Current Protocols in Cell Biology, Supplement 25, 2004, pp. 4.14.1-4.14.30.

Hess, H. et al., "PMD—New detector for fluorescence lifetime measurement," Proceedings from International Conference Optoelectronics, Optical Sensors and Measuring Techniques, May 2002, 6 pages.

Mitchell, A.C. et al., "Direct modulation of the effective sensitivity of a CCD detector: a new approach to time-resolved fluorescence imaging," The Royal Microscopical Society, Journal of Microscopy, vol. 206, Pt. 3, Jan. 2002, pp. 225-232.

Mitchell, A.C. et al., "Measurement of nanosecond time-resolved fluorescence with a directly gated interline CCD camera," The Royal Microscopical Society, Journal of Microscopy, vol. 206, Pt. 3, Jan. 2002, pp. 233-238.

Nishikata, K. et al., "Real-time lock-in imaging by a newly developed high-speed image-processing charge coupled device video camera," American Institute of Physics, Review of Scientific Instruments, vol. 74, No. 3, Mar. 2003, pp. 1393-1396.

Oggier, T. et al., "An all-solid-state optical range camera for 3D real-time imaging with sub-centimeter depth resolution (SwissRanger™)," CSEM SA, Badenerstrasse 569, CH-8048 Zurich, The Royal Microscopical Society, Journal of Microscopy, 2002, 12 pages.

Webb, S.E.D. et al., "A wide-field time-domain fluorescence lifetime imaging microscope with optical sectioning," Review of Scientific Instruments, American Institute of Physics, vol. 73, No. 4, Apr. 2002, pp. 1898-1907.

Abramowitz, et al. (Jul. 16, 2004). "Anatomy of a Charge-Coupled Device". Molecular Expressions. Retrieved Oct. 17, 2011. <http://micro.magnet.fsu.edu/primer/digitalimaging/concepts/ccdanatomy.html>.

* cited by examiner

SOLID-STATE PHOTODETECTOR PIXEL AND PHOTODETECTING METHOD

RELATED APPLICATIONS

This application is a Continuation of U.S. application Ser. No. 12/987,669, filed on Jan. 10, 2011, which is a Divisional of U.S. application Ser. No. 11/658,516, filed on Feb. 25, 2008, now U.S. Pat. No. 7,897,928, which is a 371 national phase filing of International Application No. PCT/CH2005/000436, filed on Jul. 25, 2005, which claims priority to European Patent Application No. 04405475.7, filed on Jul. 26, 2004, all of which are incorporated herein by reference in their entirety.

FIELD OF THE INVENTION

This invention relates to solid-state photodetecting, especially charge-coupled-device (CCD) photodetecting. In particular, it relates to a photodetector pixel and a photodetecting method according to the preambles of the independent claims. Possible applications of the invention lie, for instance, in range detection or in (bio-)chemical sensing.

BACKGROUND OF THE INVENTION

Solid-state one-dimensional and two-dimensional photodetectors with picture elements (pixels) based on the charge-coupled-device (CCD) principle are well-known; cf. A. J. P. Theuwissen: "Solid State Imaging with Charge Coupled Devices", Kluwer Academic Publishers, Dordrecht, 1995. They find use not only in consumer goods such as ordinary cameras, but also in combination with a dedicated light source in special applications such as time-of-flight (TOF) range cameras (cf. EP-1,152,261 A) or in (bio-)chemical sensing (cf. EP-1,085,315 A). For such special applications, the properties of standard CCD pixels may not be sufficient. The pixels perform the tasks of the photo-generation of charges, the separation of said charges and the charge accumulation of said separated charges either in at least one storage site and at least one dump site or in at least two storage sites. For the above-mentioned special applications it is also advantageous to incorporate means of repeated charge accumulation, such as described in U.S. Pat. No. 5,856,667.

An important property of such a CCD pixel is the so-called shutter efficiency. The shutter efficiency is defined as the number of photogenerated charge carriers transported to the desired accumulation site divided by the total number of photogenerated charge carriers. Using state-of-the-art technology, this quantity is in the range between 80% and 95%, which is not sufficient for special applications such as mentioned above, as will be described in the following.

SUMMARY OF THE INVENTION

It is an object of the invention to provide a photodetector pixel and a photodetecting method which provide a higher shutter efficiency and a higher sensitivity.

These and other objects are solved by the photodetector pixel and the photodetecting method as defined in the independent claims. Advantageous embodiments are defined in the dependent claims.

The pixel according to the invention is formed in a semiconductor substrate with a plane surface for use in a photodetector. It comprises an active region for converting incident electromagnetic radiation into charge carriers of a first and a second charge type, charge-separation means for generating a lateral electric potential across the active region, and charge-storage means for storing charge carriers of at least one type generated in the active region, said charge-storage means being placed outside the active region.

The pixel further comprises separation-enhancing means for additionally enhancing charge separation in the active region and charge transport from the active region to the charge-storage means.

The solid-state image sensor according to the invention comprises a plurality of pixels according to the invention, arranged in a one- or two-dimensional array.

The solid-state image sensor according to the invention is preferably used in a range camera or in a chemical and/or biochemical sensor.

The camera according to the invention comprises a solid-state image sensor according to the invention.

The method according to the invention for detecting incident electromagnetic radiation, comprises the steps of converting the incident electromagnetic radiation into charge carriers of a first and a second charge type in an active region of a semiconductor material with a plane surface, generating a lateral electric potential across the active region, and storing outside the active region charge carriers of at least one type generated in the active region. Charge separation in the active region and charge transport from the active region to the charge-storage means is additionally enhanced.

The method according to the invention is preferably used for range detection or for chemical and/or biochemical sensing.

The method according to the invention for determining a distance between a measurement system and a remote object comprises the steps of illuminating the object by modulated electromagnetic radiation emitted from the measurement system, reflecting and/or scattering at least part of the electromagnetic radiation from the object, detecting electromagnetic radiation reflected and/or scattered from the object in the measurement system, the detection using the detection method according to the invention, and determining the distance from the detected electromagnetic radiation.

The method for sensing a chemical and/or biochemical substance, comprises the steps of illuminating the substance with electromagnetic radiation, causing the electromagnetic radiation to interact with the substance directly or indirectly through a transducer, and detecting electromagnetic radiation resulting from the interaction with the substance, the detection using the detection method according to the invention.

BRIEF DESCRIPTION OF THE DRAWINGS

Embodiments of the invention are described in greater detail hereinafter relative to the attached schematic drawings.

DESCRIPTION OF PREFERRED EMBODIMENTS

Figure 1:
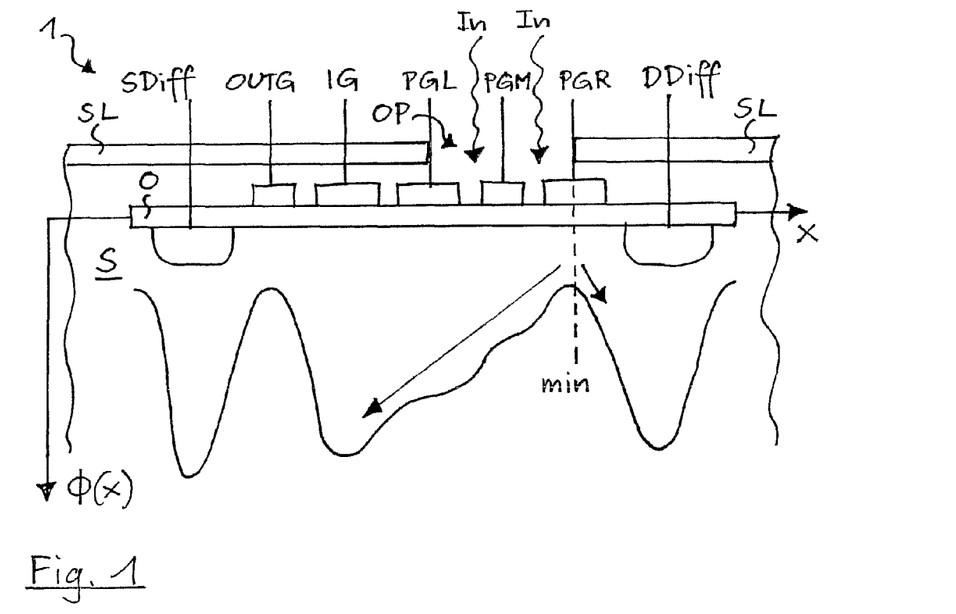
FIGS. 1 and 2 show cross-sectional views of a CCD part of a first and a second embodiment of a photodetector pixel according to the invention, respectively.

FIG. 1 shows a cross-sectional view of a CCD part of a first embodiment of a photodetector pixel 1 according to the invention. The pixel 1 comprises the well-known structures such as a left photogate PGL, a middle photogate PGM and a right photogate PGR. The region beneath the photogates PGL, PGM and PGR can be called the "active region" of the pixel, since this is the region in which incident radiation In is converted into charge carriers. The pixel 1 further comprises either at least one integration gate (IG) for storing charge carriers generated in the active region and at least one dump site (DDiff), or at least two integration gates, the integration gates (IG) and the dump-site (DDiff) being placed outside the active region. The embodiment of FIG. 1 comprises an integration gate IG, an isolation gate OUTG, a sense diffusion SDiff and a dump diffusion DDiff. All these elements PGL, PGM, PGR, IG, OUTG, SDiff, DDiff are arranged above or beneath a gate-oxide layer O on a substrate S made of, e.g., bulk silicon of the p doping type. A shield layer SL typically made of metal protects all elements except the photogates PGL, PGM, PGR from incident light In. The shield layer SL has an opening OP in the active region of the photogates PGL, PGM, PGR, so that the photogates PGL, PGM, PGR can be exposed to the incident light In passing through the opening OP.

A lateral potential distribution $\Phi(x)$ on top of the substrate S is also drawn in FIG. 1 as a function of a horizontal coordinate x. By applying proper voltages to the photogates PGL, PGM, PGR, the potential gradient in the substrate S can be influenced. In the state shown in FIG. 1, the potential under the integration gate IG is high and decreases towards the right photogate PGR, so that charge carriers generated by the incident light In are transported to the integration gate IG, where they are integrated over a certain exposure time. Although the potential distribution $\Phi(x)$ is often graphically represented as a sequence of ideal, discrete steps and/or wells, this is not the case in practice. The real potential distribution $\Phi(x)$ is rather continuous, as sketched in FIG. 1. This continuous character of the potential distribution $\Phi(x)$ results in a potential minimum min beneath the right photogate PGR. Thus, charge carriers optically generated in the region on the right-hand side of the minimum min are not transported to the integration gate IG but rather to the dump diffusion DDiff. Such an undesired electron flow substantially decreases the shutter efficiency of the pixel 1. An analogous undesired effect occurs in case that the potential $\Phi(x)$ increases from the left photogate PGL towards the right photogate PGR.

The invention avoids the above-described charge-separation imperfection by a design of the shield layer SL that takes into account the predicted real potential distribution $\Phi(x)$. In pixels known up to now, the opening in the shield layer made possible an illumination of the entire photogate area by the incident light, i.e., in the representation of FIG. 1, the edges of the shield layer coincided with the outer edges of the left and right photogates, respectively. According to the invention, however, the left and right photogates PGL, PGR are partially covered by the shield layer SL, and the edges of the shield layer SL are located on a position where the minimum min of the potential distribution $\Phi(x)$ is expected to be. This position depends on the geometry and the materials of the pixel 1 and on the voltages applied. It may be determined based on calculation. Simulation tools, typically computer software, for calculating such potential distributions $\Phi(x)$ are available.

It has been found that a shielding layer SL as shown in FIG. 1 shields well in case of normal incidence ($\alpha=0$) of light on the pixel, but not in other cases, and especially not for large incidence angles $\alpha$ of, e.g., 15° and more. This is due to the three-dimensional geometric arrangement of the gates and the shielding layer SL. The latter is placed about 4 μm (depending on the used process) above the surface of the substrate S, so that light In impinging at an angle $\alpha \neq 0$ reaches, e.g., part of the integration gate IG. This is avoided in a second embodiment of a pixel according to the invention, shown in FIG. 2. This embodiment uses, besides a topmost shielding layer SL1, other metal layers SL2, SL3, . . . , which lie closer to the substrate S as further shielding layers. Such metal layers SL2, SL3, . . . are provided, e.g., in a standard complementary-metal-oxide-semiconductor (CMOS) process for interconnecting lines. The lowermost metal layer SL3, which lies typically about 1 μm above the surface of the substrate S, defines most precisely the position on which light In will impinge, with a low degree of dependence on the angle of incidence $\alpha$.

Figure 2:
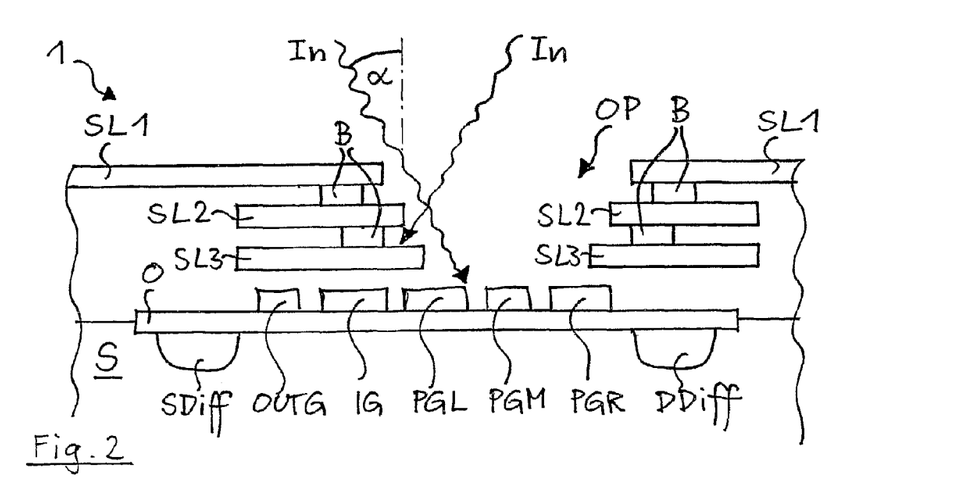

Part of the light In could be coupled between the metal layers SL1, SL2, SL3, . . . and guided to very distant points like in a waveguide. To avoid this, vertical opaque barriers B are provided. These barriers B can be designed and realized as the vias known from the standard CMOS process, i.e., as tungsten connections through the insulating interlayers between the horizontal metal layers SL1, SL2, SL3, . . . .

Figure 3A:
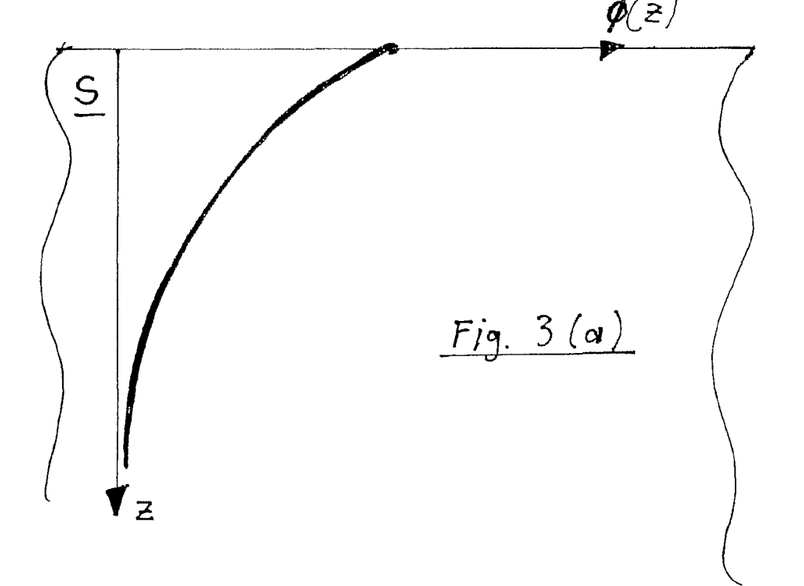
FIG. 3 shows electric potential distributions versus the vertical coordinate (a) for a pixel with a homogeneous substrate, and (b) for a pixel with a buried channel.
Figure 3B:
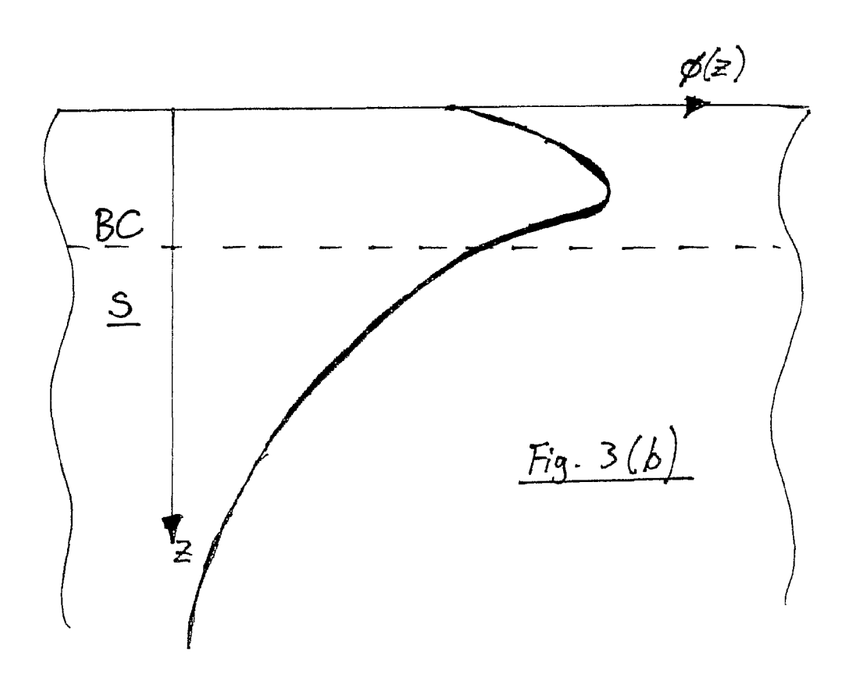

FIG. 3 shows transverse potential distributions $\Phi(z)$ in the pixel substrate S versus the vertical coordinate z for two different substrates S. In case of a homogeneous semiconductor substrate S and a positive voltage applied at the gate, the potential distribution $\Phi(z)$ has a maximum value at the surface of the substrate S and monotonically decreases with the depth z in the substrate S, as shown in FIG. 3(a). According to another embodiment of the invention, a transverse inhomogeneity BC is provided in the substrate S. Such an inhomogeneity can be realized, e.g., as a buried channel BC of an n doped material in the p bulk substrate S, with a thickness of 0.3 μm to 3 μm, and preferably about 1 μm. As schematically shown in FIG. 3(b), the potential distribution $\Phi(z)$ now has a maximum value inside the buried channel BC, which maximum value is even higher than that of FIG. 3(a). Thus, the inhomogeneity BC helps to create a high potential inside the substrate S and thus enhances and makes faster the charge separation. It also reduces noise, since flicker noise is much higher for charges moving along the substrate surface due to numerous trapping centres at the silicon/silicon-dioxide interface. This is avoided in the embodiment of FIG. 3(b).

Figure 4:
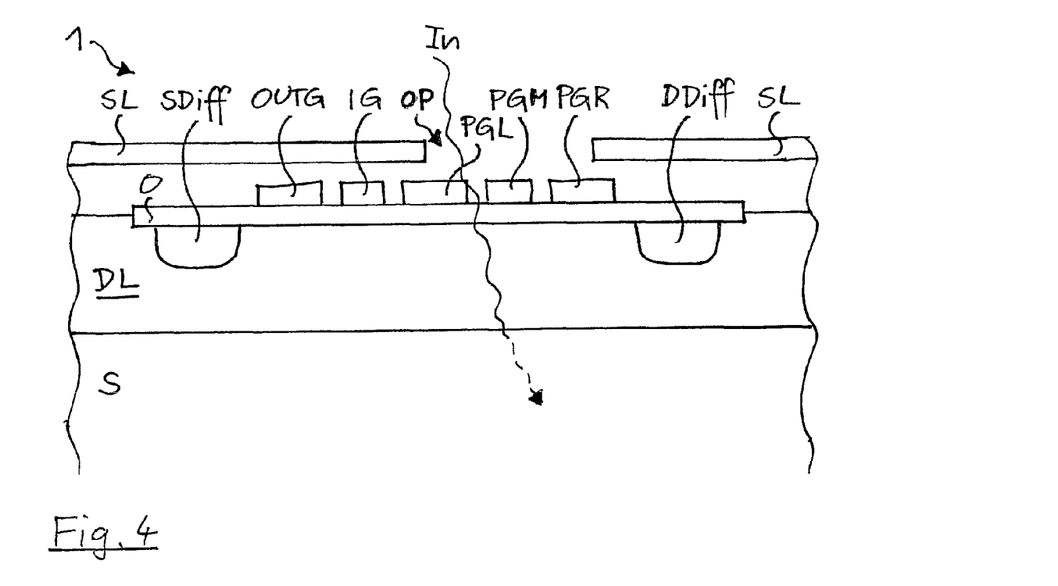
FIGS. 4 and 5 show cross-sectional views of a CCD part of a fourth and a fifth embodiment of a photodetector pixel according to the invention, respectively.

In both cases shown in FIGS. 3(a) and (b), respectively, it is noted that the electric potential Φ reaches about z≈10 μm into the silicon substrate S. Charge carriers generated in this area 0≤z≤10 μm are transported towards the potential maximum due to a vertical drift field (i.e., they are collected). However, the absorption length of red and infra-red light in silicon is up to 30 μm. Consequently, there are also charge carriers photogenerated in the deep substrate region z>10 μm without such a vertical drift field. These charge carriers are undesired, because they have first to diffuse to the potential well in order to be collected. Given that the diffusion of these charges happens in the neutral bulk, no predefined direction for this diffusion exists. Therefore, the resulting net movement cannot be predicted. It is well possible that an electron is created below one pixel, diffuses in the bulk over a net distance of several pixel pitches and is then collected by a different pixel than the one below which it was created. An embodiment of the pixel 1 according to the invention in which this problem is eliminated is shown in FIG. 4. The bulk substrate S is made of a material that impedes charge-carrier transport and/or supports charge-carrier recombination, e.g., a bad-quality and/or a highly doped silicon substrate of the p doping type. Charge carriers photogenerated in the bulk of such a substrate S are trapped by material defects and/or recombine before reaching the drift field region. In order to make possible photodetection at all, a detection layer DL of good quality and low doping is arranged on the surface of the substrate S. The detection layer DL can be, e.g., an epitaxial silicon layer with a thickness of 2 μm to 20 μm, and preferably of 5 μm to 10 μm.

Figure 5:
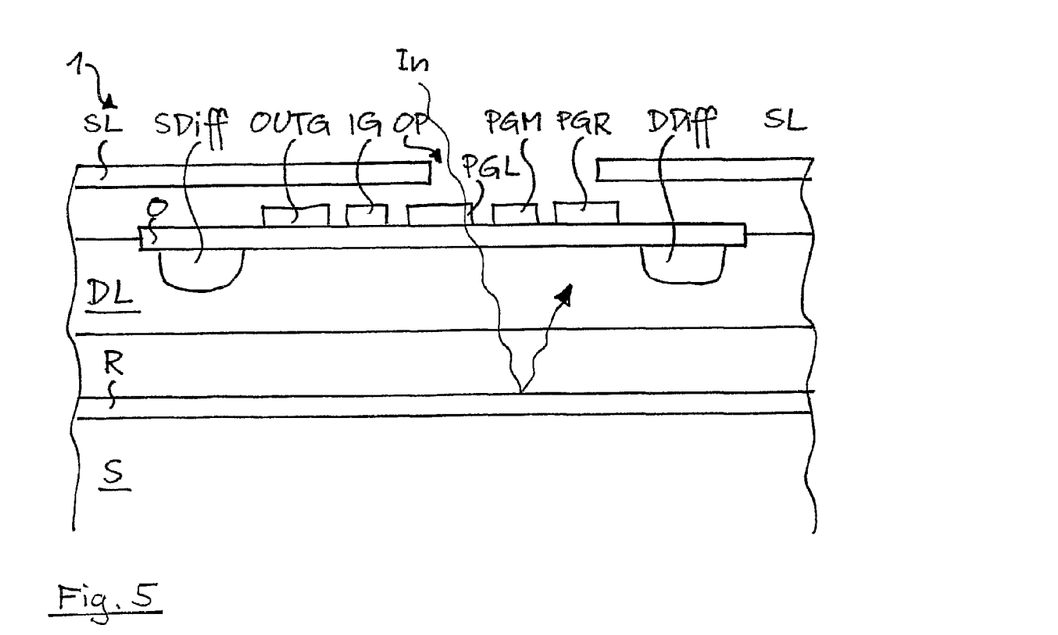

Another embodiment of the pixel 1 according to the invention which deals with the problem set forth with reference to FIG. 4 is shown in FIG. 5. In contrast to the embodiment of FIG. 4, light In is prevented from penetrating into deeper regions of the substrate S, or even reflected back from deeper regions of the substrate S into a region DL beneath the substrate surface, where it can be used for the photodetection process. For this purpose, an opaque and/or reflecting layer R is provided in the substrate S between said detection layer DL (epitaxial layer) and the highly doped bulk S. The opaque and/or reflecting layer R can be a metal layer, e.g., an aluminum layer and/or a silicon dioxide layer. In the first case (with a metal layer), the metal layer has to be electrically isolated from the detection layer DL. The preferred configuration in this case is a silicon absorption layer on top, a silicon dioxide layer for the isolation and the metal layer for the reflection. In the second case (without a metal layer), the substrate S is preferably a silicon-on-insulator (SOI) substrate, i.e., a silicon substrate with an oxide layer buried in it.

One preferred application of the pixel 1 according to the invention is in a solid-state time-of-flight (TOF) range camera. The inventive methods described in the following are suitable for use in such a camera.

A first embodiment of a photodetecting method according to the invention relates to a TOF range camera, the pixels of which have at least one active region and at least two (e.g., four) charge storages for on-pixel driving voltage control or at least one charge storage for off-pixel driving voltage control, which are used to store the different charge types. The demodulation of a modulated light signal can be obtained, e.g., by storing the different charge types deriving from different phases (e.g., 0°, 90°, 180° and 270°).

Figure 6:
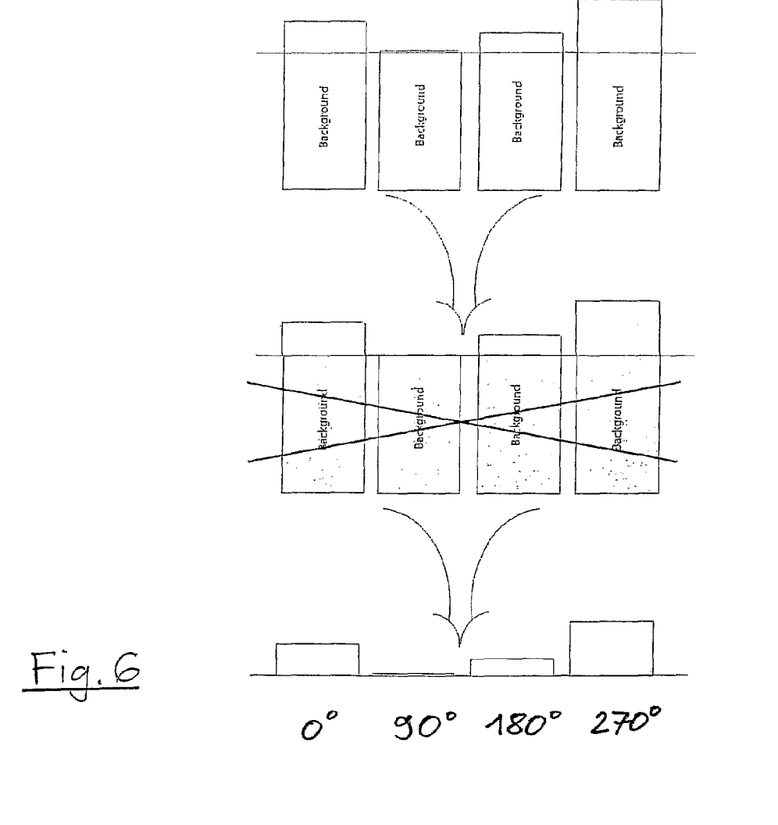
FIG. 6 shows the principle of adaptive background suppression (or minimal charge transfer).

In a CCD pixel, the photogenerated charge is converted to an output voltage by the storage capacitance. It has been found that the storage capacitance of the integration gate IG is by factors higher than the capacitance of the sense diffusion SDiff. Therefore, the limiting storage capacitance is given by the sense diffusion SDiff and not by the integration gate IG. However, the readout capacitance cannot be designed arbitrarily high because of noise restrictions and the resolution of the analog-to-digital conversion. The main restriction of dynamic range is given by background illumination. The background usually generates for all light-sensitive areas an equal amount of charge carriers that are not needed for the distance calculation. The inventive concept consists in taking into account only those charge carriers which contribute to the difference. In other words: a constant offset is subtracted from all signals. This is schematically illustrated in FIG. 6. With thus reduced signals, a smaller readout capacitance can be used and, even so, acceptable output voltage signals are obtained.

Figure 7:
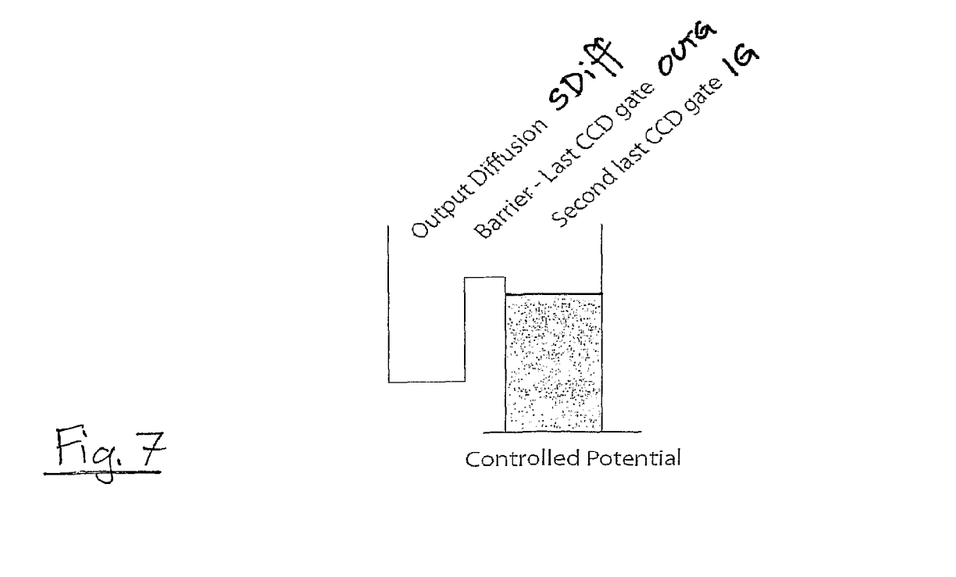
FIG. 7 shows the lateral potential distribution for the sense diffusion, the isolation gate and the integration gate of a photodetector pixel.

FIG. 7 schematically shows the lateral potential distribution Φ(x) for the sense diffusion SDiff, the barrier-last CCD gate (the isolation gate OUTG) and the second last CCD gate (the integration gate IG, charge storage) of a photodetector pixel 1 as shown in FIG. 1. The above-mentioned offset subtraction is performed by transferring not all the charge carriers from the integration gate IG to the sense diffusion SDiff, but only those charge carriers which are necessary to perform correct distance calculations. After having collected all charge carriers on the integration gate IG, its control voltage is decreased to such a level for which every sense node Sdiff receives charge carriers. The isolation gate OUTG then pinches off the remaining charge carriers which are of the same amount for all photosensitive areas. Thus, the differential functionality is ensured.

Figure 8:
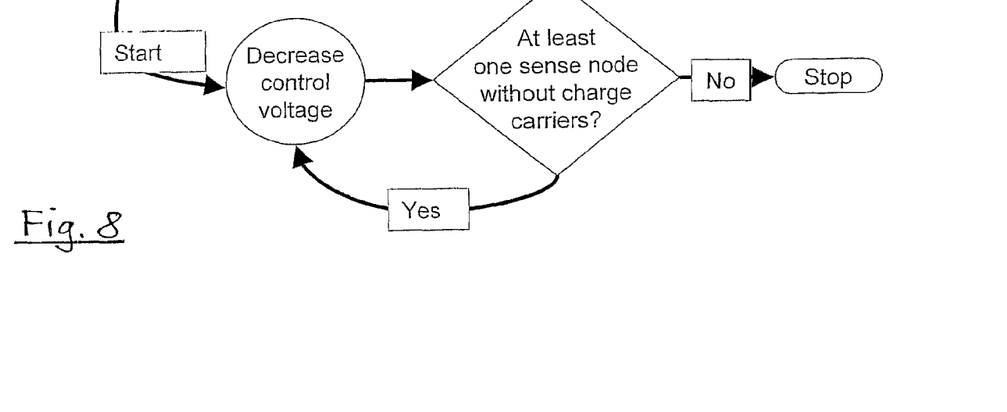
FIG. 8 shows a flow diagram of a first embodiment of the photodetecting method according to the invention.

The appropriate driving voltage for the integration gates IG can be adjusted on-pixel by a closed loop from the sense nodes to the driving voltage, as shown in the flow chart of FIG. 8. By implementing appropriate integrated circuits, the loop can be performed pixelwise. Alternatively, the potential of the integration gate IG can be stepwise decreased and the pixel can be read out off-pixel until all samplings obtain a signal. This requires a non-destructive readout or a summing function off-pixel.

Figure 9:
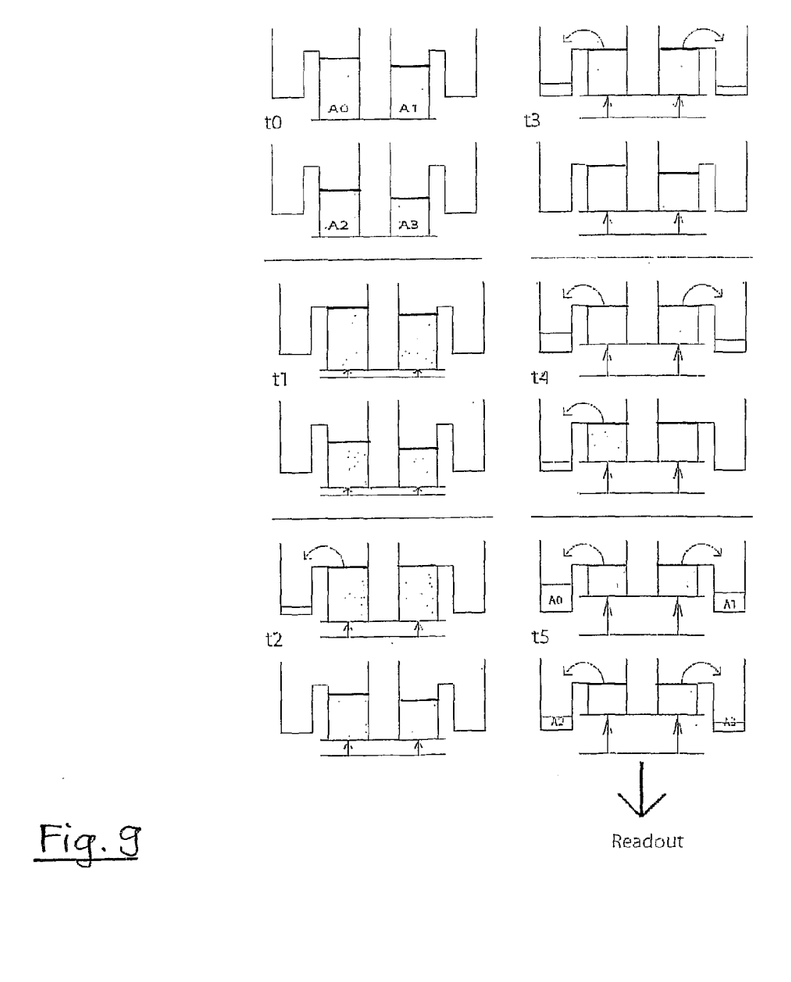
FIG. 9 shows the method of FIG. 8 in an analogous representation as FIG. 7, for different times.

FIG. 9 illustrates the adaptive background subtraction for a pixel 1 with four photosensitive areas corresponding to the phases 0°, 90°, 180°, 270° (cf. FIG. 6), for six different, subsequent times t0-t5. It illustrates the on- as well as off-pixel background pinch off. Thus, the dynamic range is increased, and high accuracies are possible due to longer possible integration times.

Figure 10:
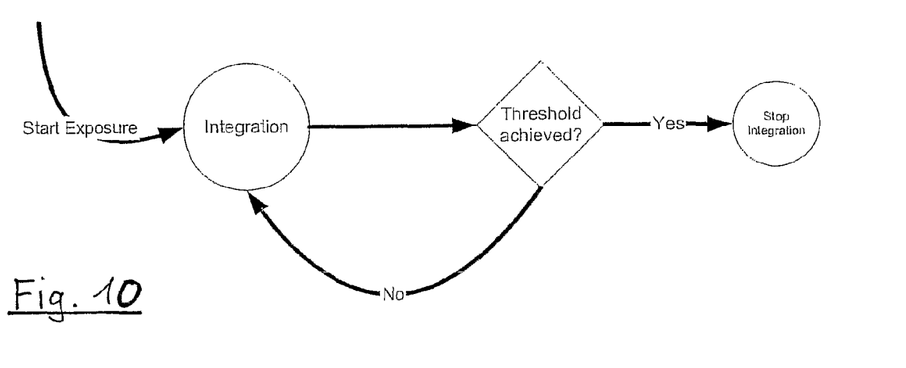
FIGS. 10 and 11 show flow diagrams of a second and a third embodiment of the photodetecting method according to the invention.

A second embodiment of a photodetecting method according to the invention also relates to a TOF range camera with at least one photosensitive area and a plurality of charge storage areas. This embodiment takes into account the possibility of providing a feedback loop from the sense node to the integration gate, and is based on the recognition that for a range measurement, an absolute intensity value (and thus an absolute integration time) is not important, since only a phase information is extracted from the plurality of storage areas of a pixel. Therefore, different pixels can have different integration times, as long as the integration time is the same for all charge storage areas within each pixel. The integration time for an individual pixel is preferably chosen such that it yields a high signal just below the saturation level. Thus, the dynamic range is increased. A flow diagram of the method is shown in FIG. 10.

Figure 11:
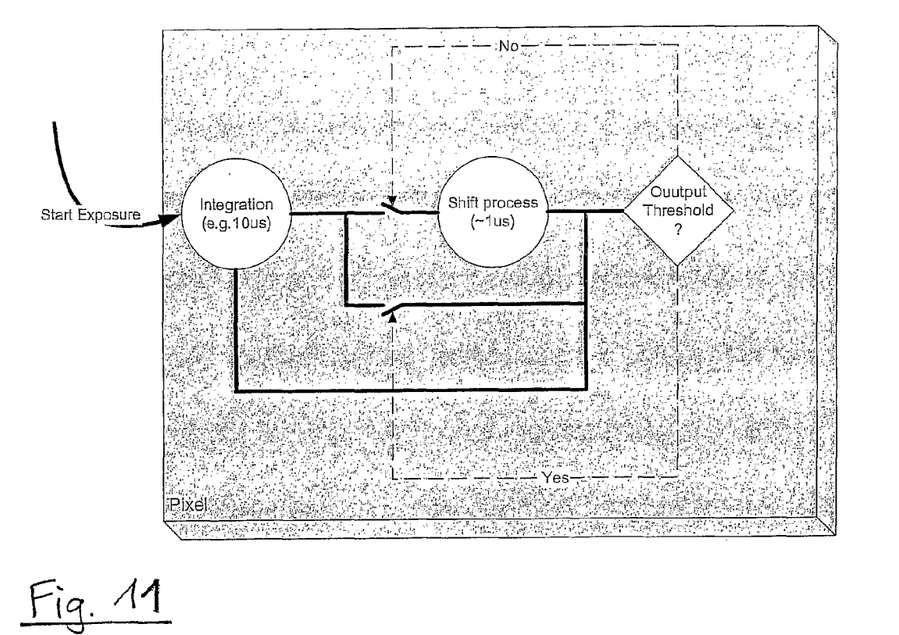

In the known TOF pixels, a barrier (the isolation gate OUTG) prevents the charge carriers from drifting from the integration gate IG to the sense node SDiff. During integration, all charge carriers are kept back in the integration well and only after exposure they are transferred to the output node SDiff in the so-called shift process. Due to this behaviour, a continuing monitoring of the sense nodes SDiff is not possible. By contrast, in the method according to the invention, the shift process is performed during integration in short shift intervals until a given threshold close to saturation is reached. A simplified flow diagram of this embodiment is shown in FIG. 11. In this example, a longer integration interval of, e.g., 5 to 200 µs, is followed by a shorter shift interval of, e.g., 1 µs. This loop is repeated as long as the output of each photosensitive area is smaller than a certain threshold. When the output reaches the threshold, the shift process will not be performed any longer, so that saturation at the sense node SDiff is avoided.

Figure 12:
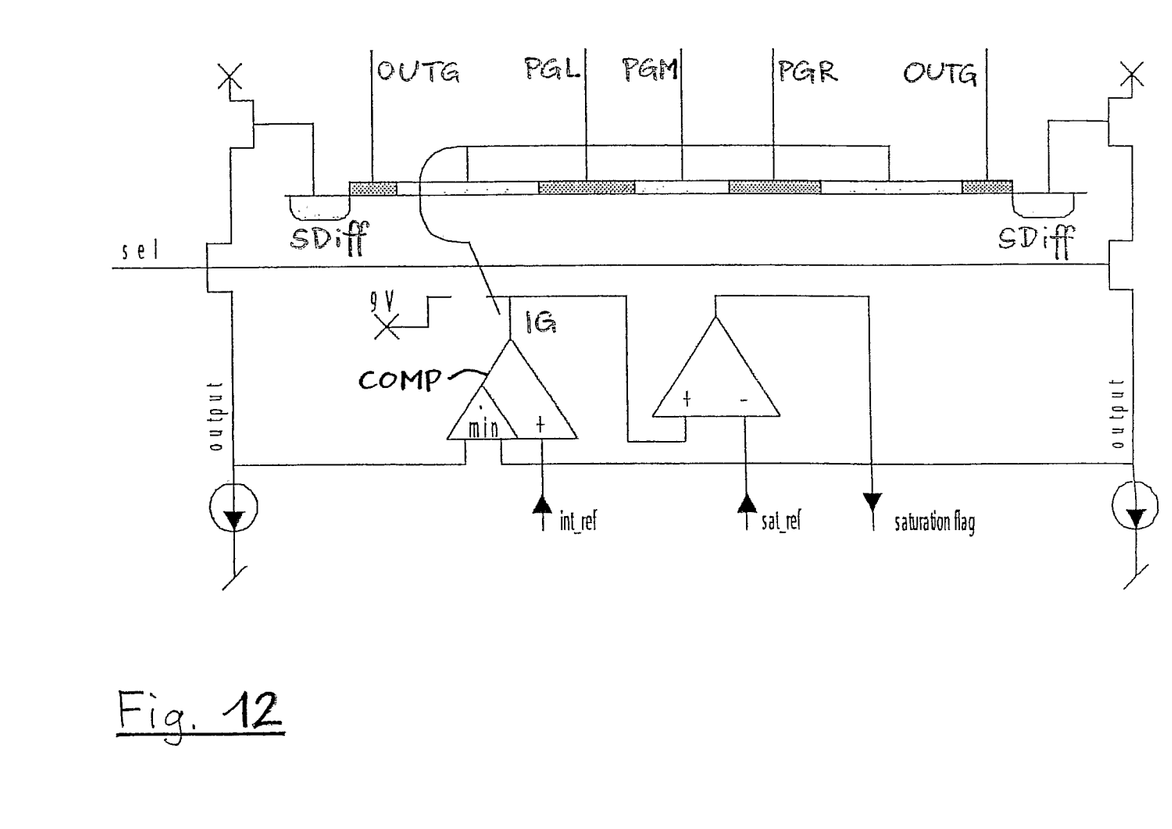
FIG. 12 shows a diagram for performing the first embodiment of the photodetecting method according to the invention.

FIG. 12 shows a simple circuit diagram for performing the photodetection method according to the invention. The output signals from the sense nodes or sense diffusions Sdiff are fed into a comparator COMP, where they are compared with a decreasing control voltage int_ref for the integration gate IG. The output of the comparator COMP is used as the decreasing potential applied to all integration gates IG. A saturation flag is set when the potential of the integration gates IG falls below a certain value predetermined by a reference signal sat_ref.

In addition to the information obtained from the sampling signals, i.e., the amounts of charges from the sense diffusions SDiff (cf. FIG. 7), the potential of the integration gate IG can be read out as a further quantity to be measured. This quantity corresponds to the DC offset value common to the charges accumulated in all integration gates IG of a pixel. From this quantity, further information can be extracted, e.g., the level of the background illumination and/or whether an overflow of at least one integration gate IG occurred during the charge-storage process.

A third embodiment of a photodetecting method according to the invention also relates to a TOF range camera comprising a plurality of photosensitive areas. This method allows to control whether a pixel 1 is intact and works correctly. The idea is to create redundancy by performing at least two measurements of the same scene, however, with different phases of the emitted CW-modulated light. A phase shift of δ 1 (in degrees) introduces an artificial distance shift of $$\Delta L = \frac{\delta}{360°} \cdot \frac{c}{2f},$$

wherein c≈3·10⁸ m/s is the light velocity in air and f is the modulation frequency. In an example where f=20 MHz and δ=180°, an artificial distance shift of ΔL=3.75 m should be obtained. If this is not the case for a certain pixel, said pixel is faulty.

Another preferred field of application of the pixel according to the invention is (bio-)chemical sensing. Some examples for such applications are given in the following.

A first application concerns (bio-)chemical sensors using luminescent labels. Two general measurement methods aiming at reaching high sensitivity apply, namely time-domain and frequency-domain measurements, such as described in "Elimination of Fluorescence and Scattering Backgrounds in Luminescence Lifetime Measurements Using Gated-Phase Fluorometry" by H. M. Rowe et al., Analytical Chemistry, 2002, 74(18), 4821-4827, and in "Principles of Fluorescence Spectroscopy", by Lakowicz J., Kluwer Academic and Plenum Publishers, New York, pages 1-24 (1999), respectively. In frequency-domain measurements, the luminescent sample is excited with periodically modulated light, and the detection of luminescent emission occurs at the same frequency. This measurement method is often referred to as "lock-in technique". The second measurement method uses repeated excitation using short pulses, with subsequent detection of the luminescent emission inside a different time window. This method is often referred to as "time-gated detection". Both measurement methods may be used for the determination of luminescent intensity and/or lifetime. All measurement methods cited above and combinations thereof will profit from the present invention through the properties of parallel detection combined with on-chip implementation of signal treatment, the latter leading to a lower detection limit in comparison to conventional imaging systems.

Figure 13:
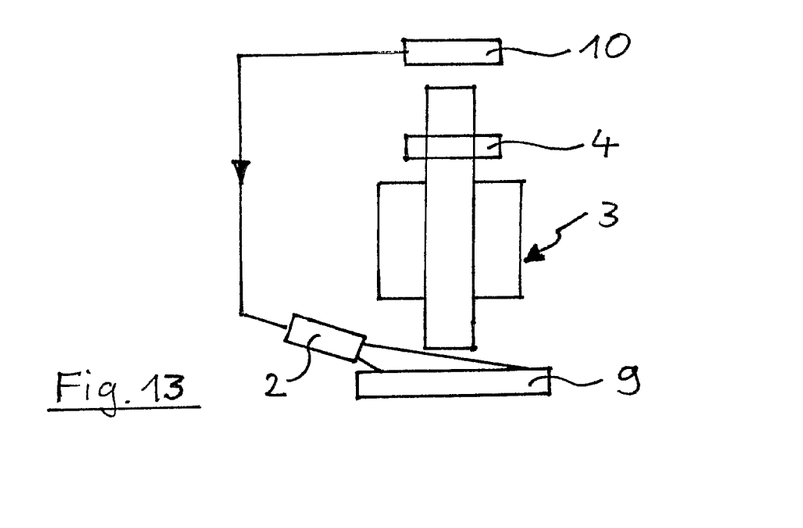
FIGS. 13-16 show setups for four application examples for the camera according to the invention.

A first example for practical implementation is luminescence imaging, e.g., fluorescence microscopy, using the general measurement methods described above. A fluorescence-microscopy setup with a sample 9, a modulated light source 2, a microscope 3, a wavelength filter 4 and a camera 10 according to the invention is schematically shown in FIG. 13. The camera 10 comprises an image sensor comprising an array of pixels 1 according to the invention. The light source 2 is triggered by the camera 10. The advantages over other detection methods are that imaging of the sample 9 and parallel detection of the luminescence signals are possible with a low detection limit. Compared to other imaging methods, the inventive method described above yields a higher sensitivity and a lower detection limit.

Figure 14:
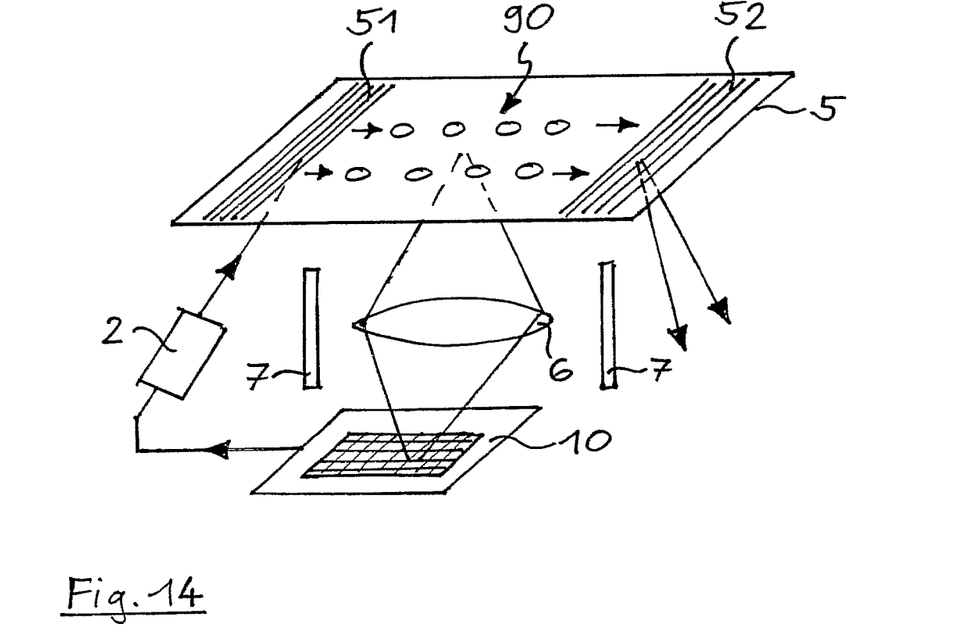

Another application example of the camera 10 according to the invention in the field of biochemical sensing is the readout of a sensor microarray 90. The microarray 90 may be arranged on a planar waveguide 5, as shown in FIG. 14. A light source 2, e.g., a laser, emits light onto an input grating 51 on the waveguide 5. The light is coupled into the waveguide 5 and guided to the microarray 90, where its evanescent portion excites luminescence. The microarray 90 is imaged onto the camera 10 by an optical imaging system 6. Thus, a part of the luminescent light is received by the camera 10. The general luminescent measurement methods described above may be used by modulating the light source 2 and triggering it by the camera 10. Another part of the luminescent light is coupled into the waveguide 5 and propagates towards an output grating 52 where it is coupled out. This part can also be detected, as is known from the prior art. The measurements by the camera 10 according to the invention and by the conventional outcoupling approach may be combined in order to efficiently suppress the excitation light. Shielding means 7 are preferably provided for shielding the camera 10 from undesired scattered light. The advantage of this setup over existing, highly sensitive schemes is that parallel detection of part of or the whole microarray 90 is possible due to the camera 10 according to the invention.

Figure 15:
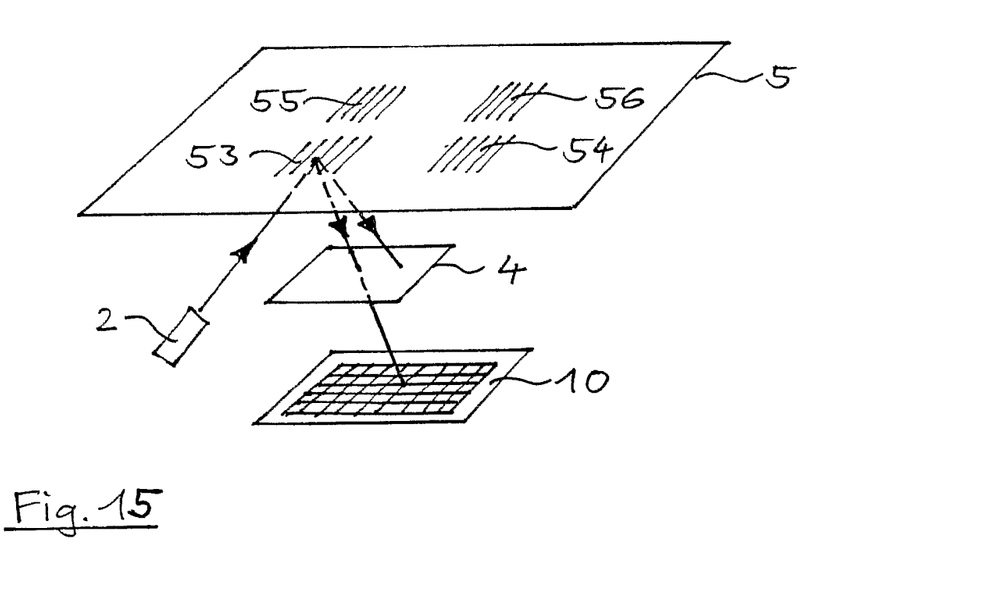

In still another example shown in FIG. 15, samples to be sensed are deposited on sensing pads or measurement units arranged on a planar waveguide 5. Each sensing pad comprises a diffraction grating 53-56. Light from a light source 2 is coupled into the waveguide 5 in the region of a sensing pad by the corresponding diffraction grating 53, excites luminescence in the sample, and the luminescent and the excitation light are coupled out by the same diffraction grating 53. A wavelength filter 4 is preferably arranged in the path of the outcoupled light in order to suppress the excitation light. However, since such a suppression will never be perfect, use of the camera 10 according to the invention is of great advantage. Instead of using a single grating, each measurement unit may comprise a pair of input and output coupling gratings.

While the previous four examples concerned luminescence sensing methods, the following examples concern label-free sensing methods.

Figure 16:
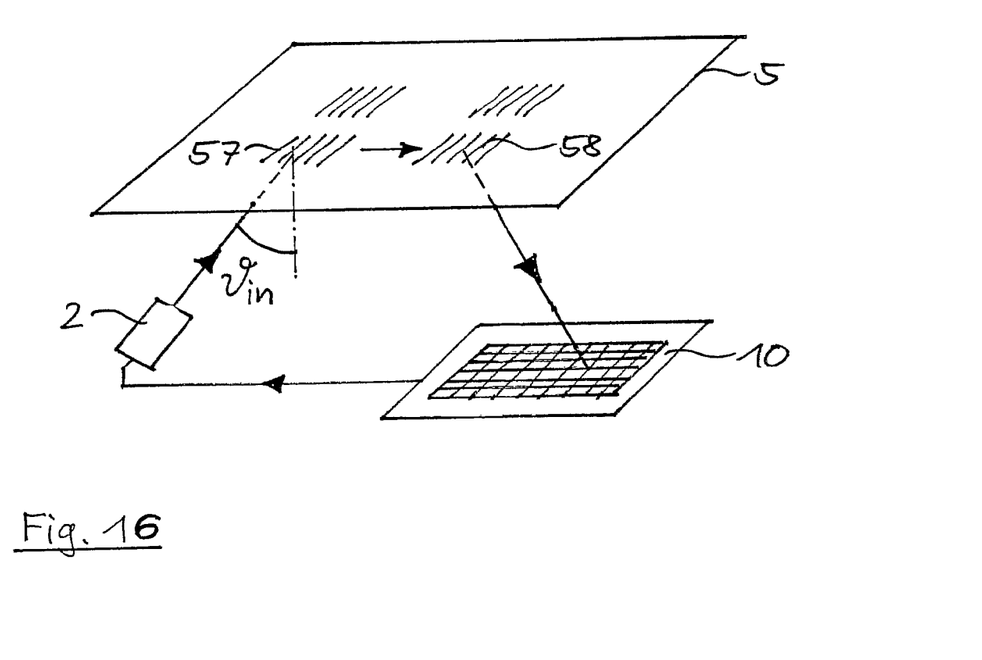
Figure 17:
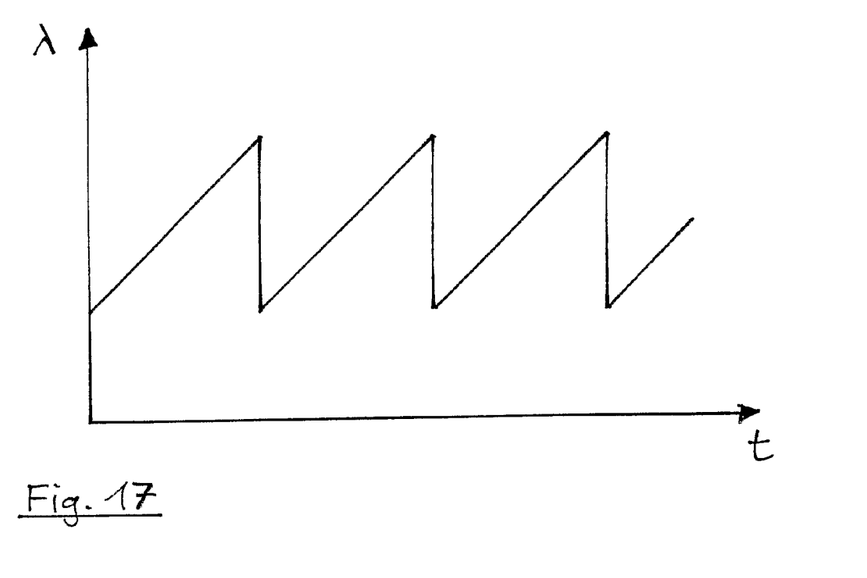
FIG. 17 shows a light-wavelength modulation as applied in the example of FIG. 16, versus time.
Figure 18:
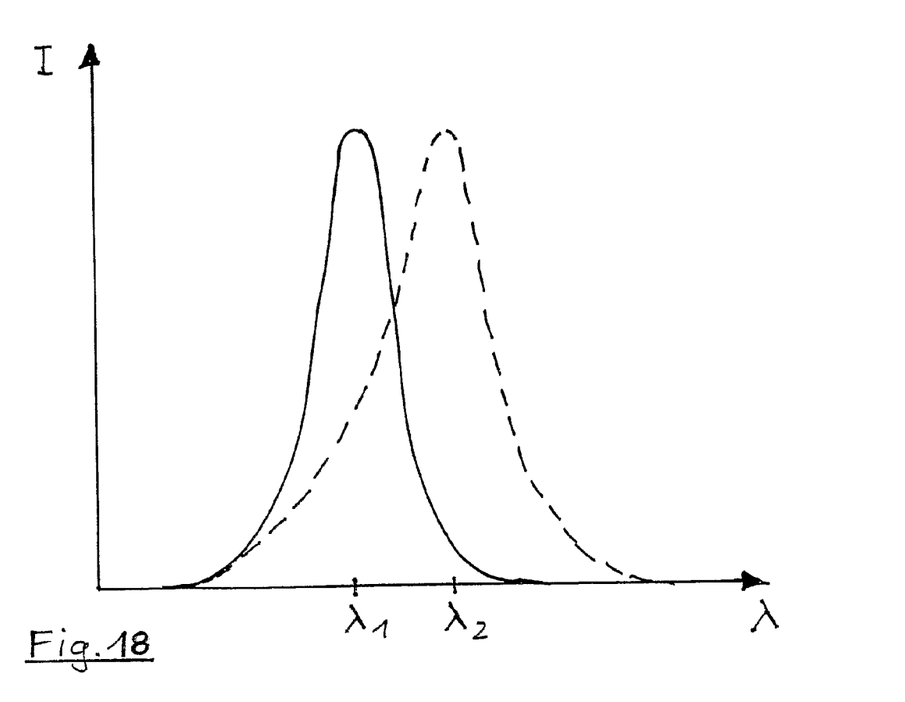
FIG. 18 shows a diagram of the intensity vs. the light wavelength as measured in the setup of FIG. 16, for two different samples.

The setup of a fifth application example of the camera 10 according to the invention in the field of biochemical sensing is shown in FIG. 16. A planar waveguide is provided with pairs of diffraction gratings 57, 58. A first grating 57 of each pair is used as the input grating and is comprised in a sensing pad for a sample to be sensed, whereas a second grating 58 of each pair is used as the output grating. Modulated light emitted by a light source 2 is incoupled into the waveguide 5 under a certain angle $\theta_{in}$. As indicated in FIG. 17, the wavelength $\lambda$ of the emitted light is modulated, e.g., periodically swept over a certain range. This is possible, e.g., with a vertical-cavity surface-emitting laser (VCSEL) as a light source 2. The modulation is triggered by the camera 10. A resonance, i.e., an intensity peak is detected at a certain wavelength $\lambda_1$ that fulfils the well-known incoupling condition for input gratings on planar waveguides, as shown in FIG. 18. When a change in the optical properties of the sample occurs, e.g., when additional molecules are deposited, the intensity peak is shifted from the first wavelength $\lambda_1$ to a second, different wavelength $\lambda_2$. Thus, information about the optical properties of the sample is obtained. This method allows imaging of the output grating 58 and is cost-effective compared to other wavelength-interrogated optical-sensing (WIGS) methods. It can be combined with a luminescence-sensing method.

Using the lock-in properties of the camera 10 according to the invention, the detection occurs at the same frequency as the wavelength sweep of the light source 2. The wavelength peak position translates therefore into an equivalent phase, which is calculated by the camera 10 based on the individual samples acquired inside the acquisition period. It can be calculated for instance using the known formalism for sinusoidal signal modulation, as it is also used for distance measurements (see, for instance, the article "Solid-State Time-Of-Flight Range Camera" by R. Lange et al., published in IEEE Journal of Quantum Electronics, No. 37, 2001, pp 390ss).

Figure 19:
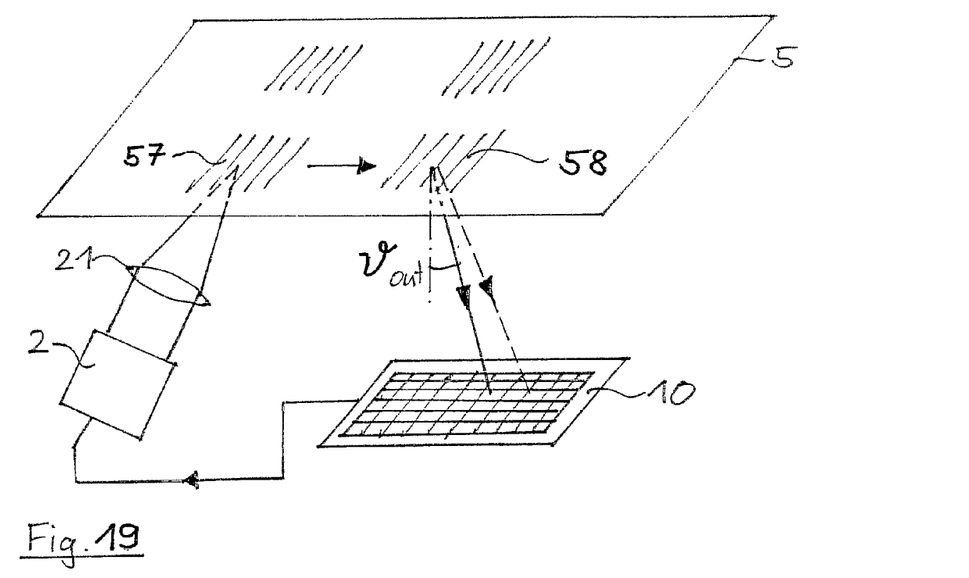
FIG. 19 shows a setup for a fifth application example for the camera according to the invention.

A still further application example of the camera 10 according to the invention in the field of biochemical sensing is discussed with reference to FIG. 19. The setup is similar to that of FIG. 16, with the differences mentioned in the following. The light emitted by the light source 2 is distributed over a certain range of angles of incidence $\theta_{in}$, e.g., by a collimating lens 21, such that light is always coupled into the waveguide 5. The sensing pad is on the output grating 58, not on the input grating 57. Since the outcoupling angle $\theta_{out}$ depends on the wavelength $\lambda$, the outcoupled light beam periodically sweeps over the camera 10. Hence, at a given position $a_1$ on the camera 10, i.e., for a given pixel, the maximum intensity I occurs at a given time, characterized by an equivalent phase when using the lock-in properties of the camera 10 as described above; cf.

Figure 20:
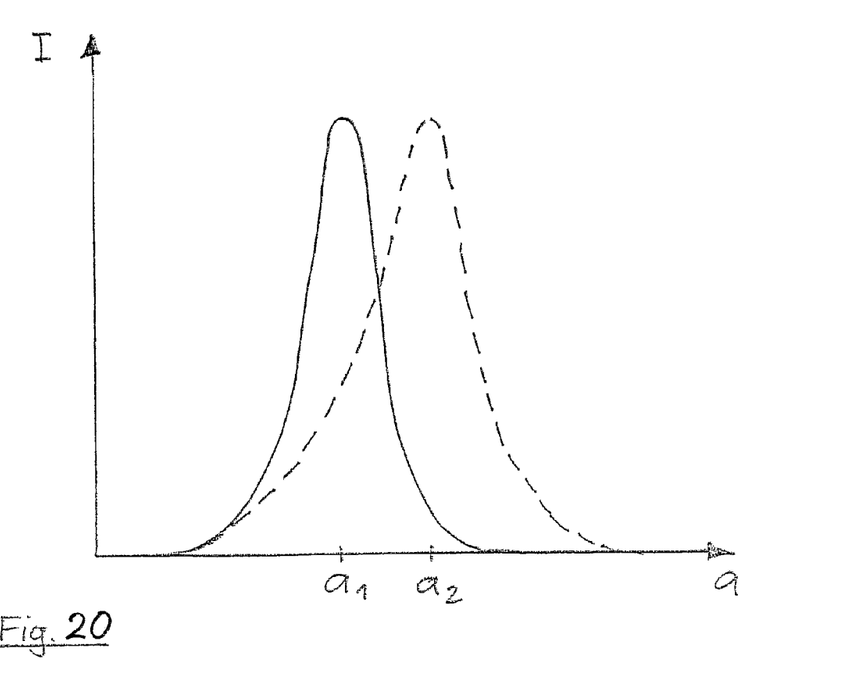
FIG. 20 shows a diagram of the intensity vs. the position as measured in the setup of FIG. 16, for two different samples.

FIG. 20. This results in a characteristic phase distribution on the camera 10. A change in the optical properties of the sample results in a shift of the intensity maximum from position $a_1$ to another position $a_2$, and eventually in a shift of the phase distribution. Thus, information about the optical properties of the sample is obtained. Compared to the WIOS method discussed above, this method offers an increased measurement range.

Figure 21:
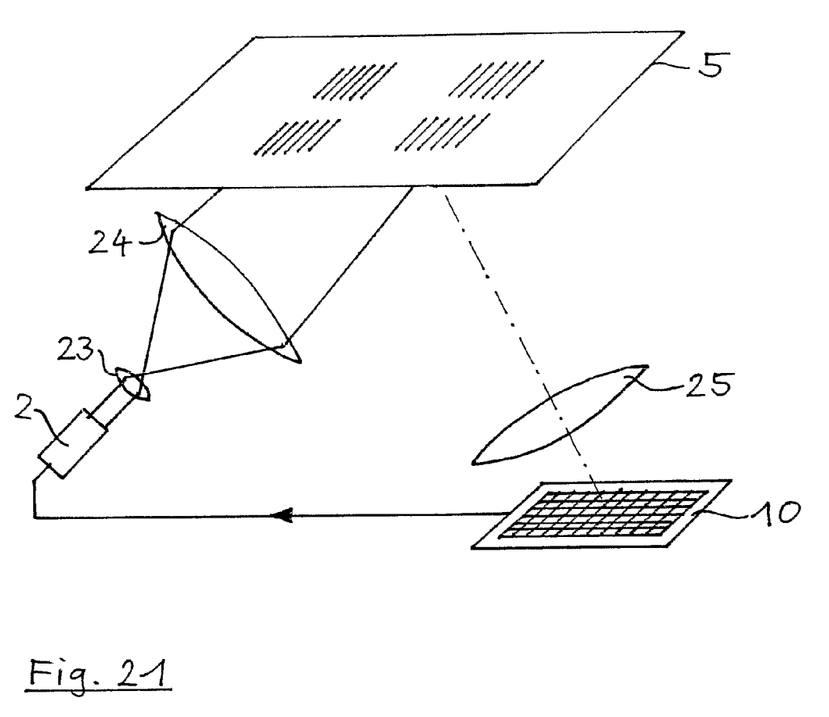
FIG. 21 shows a setup for a sixth application example for the camera according to the invention.

In the above-mentioned drawings and descriptions, only one sensing pad is considered for the sake of clarity. However, in preferred embodiments, multiple (even many or all pads of one or several chips) can be illuminated at the same time (by the same source 2), and different pixels or regions on the camera 10 are used to derive the plurality of output signals from the plurality of sensor pads quasi-simultaneously. FIG. 21 shows an embodiment of the apparatus according to the invention in which all sensing pads or gratings of the waveguide 5 are illuminated by the light source 2, e.g., by means of an optical system 23, 24 for widening the light beam and offering a limited range of incident angles to the gratings. All sensing pads or gratings or the waveguide 5 are imaged, e.g., by means of imaging optics 25, onto a photodetector chip 10 with an integrated array of lock-in pixels forming a lock-in camera. The camera is connected to the light source 2 as described above. The relevant phase information is extracted at the pixel level of the camera.

Thus, parallel processing and readout of the whole sensor chip 5 is possible.

This invention is not limited to the preferred embodiments described above, to which variations and improvements may be made, without departing from the scope of protection of the present patent. In particular, various embodiments of the invention may be combined with each other. Such a combination may yield an even better improvement than a single embodiment of the invention as described above.

LIST OF REFERENCE SIGNS

1 Pixel
10 Camera
2 Light source
21 Colimating lens
23, 24 Optical system
25 Imaging optics
3 Microscope
4 Wavelength filter
5 Planar waveguide
51 Input grating
52 Output grating
53-56 Diffraction gratings
57 Input grating
58 Output grating
6 Imaging system
7 Shielding means
9 Sample
91 Sensor microarray
a Position on camera
B Vertical opaque barrier
BC Transverse inhomogeneity, buried channel
COMP Comparator
DDiff Dump diffusion
DL Detection layer
I Intensity of light
IG Integration gate
In Incident electromagnetic radiation
int_ref Control voltage for integration gate
min Potential minimum
O Oxide layer
OP Opening in shielding layer
OUTG Isolation gate
PGL Left photogate
PGM Middle photogate
PGR Right photogate
R Opaque and/or reflecting layer
S Substrate
sat_ref Reference signal for saturation
SDiff Sense diffusion
SL Shielding layer
t Time
x Horizontal (lateral) coordinate z Vertical (transverse) coordinate
α Angle of incidence of radiation
θ Incoupling or outcoupling angle
λ Wavelength of light
Φ Potential distribution

The invention claimed is:

1. A pixel formed in a semiconductor substrate, comprising: an active region for converting incident electromagnetic radiation into charge carriers of a first and a second charge type, photogates for generating a lateral electric potential across the active region, charge storage areas for storing charge carriers of at least one said type generated in the active region, said charge storage areas being placed outside the active region, and at least two metal layers for shielding the charge storage areas with an insulating interlayer between them, the metal layers being arranged in different distances from a surface of the substrate, and one above the other and being terraced.

2. A pixel according to claim 1, wherein at least one of the metal layers projects over part of the active region.

3. A pixel according to claim 1, wherein at least one of the metal layers projects over part of the active region to expose the first section to the incident radiation and shields the second section from the incident radiation.

4. A pixel according to claim 1, wherein a vertical opaque barrier is arranged above the charge-storage areas for shielding the charge storage areas from incident radiation with non-normal incidence.

5. A pixel according to claim 4, wherein the vertical opaque barrier comprises insulating interlayer between the metal layers.

6. A pixel according to claim 4, wherein vertical opaque barriers are made of metal and are provided between the metal layers.

7. A pixel according to claim 1, wherein a transverse inhomogeneity is provided in the semiconductor substrate, to create an increased electric potential inside the substrate.

8. A pixel according to claim 7, wherein the transverse inhomogeneity is a buried channel.

9. A pixel according to claim 1, comprising a combination of a bulk substrate made of a material that impedes charge-carrier transport and/or supports charge-carrier recombination, and a detection layer made of a material that supports charge-carrier transport and/or impedes charge-carrier recombination, arranged on the surface of the substrate.

10. A pixel according to claim 9 wherein the detection layer is an epitaxial silicon layer with a thickness of 2 μm to 20 μm.

11. A pixel according to claim 1, comprising an opaque and/or reflecting layer.

12. A pixel according to claim 11, wherein the substrate is a silicon-on-insulator substrate and the opaque and/or reflecting layer is arranged beneath the insulator layer.

13. A pixel according to claim 1, further comprising a processing unit for subtracting an offset that is constant for all charge storage areas from the number of charge carriers stored in each charge storage area.

14. A pixel according to claim 13, wherein the processing unit applies a variable electric potential to a plurality of integration gates, and detects whether each integration gate yields charge carriers.

15. A pixel according to claim 14, wherein the processing unit applies a variable electric potential to a plurality of integration gates, and detects whether an output of at least one integration gate is below saturation.

16. A solid-state image sensor comprising a plurality of the pixels as described in claim 1, arranged in a two-dimensional array.

17. The image sensor according to claim 16, wherein the image sensor is of the charge-coupled-device type, and is manufactured by a complementary-metal-oxide-semiconductor process.

* * * * *